United States Patent

Kaiser

[11] Patent Number: 5,942,272
[45] Date of Patent: Aug. 24, 1999

[54] ORGANOLEPTIC COMPOSITIONS

[75] Inventor: Roman Kaiser, Uster, Switzerland

[73] Assignee: Givaudan-Roure (International) SA, Vernier-Geneve, Switzerland

[21] Appl. No.: 08/791,342

[22] Filed: Jan. 31, 1997

Related U.S. Application Data

[63] Continuation of application No. 08/440,733, May 15, 1995, abandoned.

[30] Foreign Application Priority Data

May 26, 1994 [CH] Switzerland .............................. 1633/94

[51] Int. Cl.$^6$ ....................................................... A23L 1/22
[52] U.S. Cl. ............................ 426/533; 424/49; 426/534; 426/650
[58] Field of Search ..................................... 426/533, 534, 426/650; 424/49, 58

[56] References Cited

FOREIGN PATENT DOCUMENTS 27 19 735  11/1977  Germany .

OTHER PUBLICATIONS

Svensson et al., "Marketing Pheromones of Alpinobombus Males," *Journal of Chemical Ecology*, vol. 5, No. 4, pp. 603–615 (1979).

Svensson et al., "Volatile Marking Secretions From the Labial Gland of North European Pyrobombus D. T. Males (Hymenoptera, Apidae), " *Insectes Sociaux, Paris*, vol. 24, No. 2, pp. 213–224 (1977).

Abstract of Svensson et al., *Zoon, Suppl.*, Suppl. 1, pp. 61–65 (1973).

Shirley et al., "Synthesis of 'Pre–Presqualene', a Predicated Intermediate Presqualene Biosynthesis, and of Prenylogues," *Tetrahedron Letters*, vol. 23, No. 14, pp. 1501–1504 (1982).

Boulton et al., "Mechanism of Formulation of Natural Cyclopropanes: Synthesis of Postulated Intermediates in Presqualene and Chrysanthemyl Alcohol Biosynthesis," *Chem. Soc. Perkin Trans I*m pp. 1817–1824 (1986).

Baaliouamer, A. et al., "Qualitative and Quantitative Analysis of Petitgrain Eureka Lemon Essential Oil by Fused Silicia Cappillary Column Gas Chromatography Mass Spectrometry," *J. Sci. Food Agric.*, 1985, 36, 1145–1154.

Alan M. Thomas and Michael Ozainne, "New Sesquiterpene Alcohols from Galbanum Resin: the Occurrence of C(10)–epi–Sesquiterpenoids," *Helvetica Chimica Acta*, vol. 61, Fasc. 8 (1978) Nr. 272, pp. 2874–2880.

Webster's Ninth New Collegiate Dictionary, 1983, Merriam Webster Inc., Springfield, MA, pp. 502, 832.

S. Arctander, *Perfume and Flavor Chemicals I*, (1969), item 1378 and 2897, (Montclair, NJ, 1969).

Baaliouamer et al., 1986: 95244 Document No. 104: 95244, J. Sci. Food Agric, 36(11), 1145–54, 1985. Abstract.

Thomas et al., 1979: 138041 Document No. 90: 138041, Helv. Chim. Acta., 61(8), 2874–80, 1978. Abstract.

*Primary Examiner*—Leslie Wong
*Attorney, Agent, or Firm*—Mark E. Waddell; Bryan Cave LLP

[57] ABSTRACT

A compound of the formula

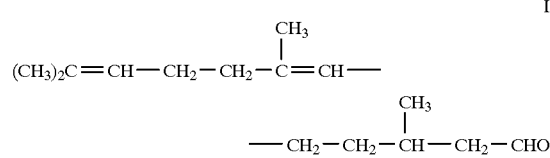

used as an odorant and/or flavorant and organoleptic compositions employing same.

19 Claims, No Drawings

ORGANOLEPTIC COMPOSITIONS

This is a continuation of U.S. application Ser. No. 08/440,733, filed May 15, 1995, now abandoned.

SUMMARY

The invention is concerned with terpene derivatives of the formula

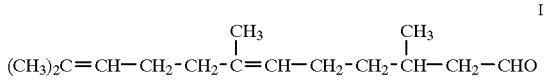

used as odorants and/or flavorants, as well as with organoleptic, odorant and/or flavorant, compositions employing same.

DETAILED DESCRIPTION

Formula I is intended to embrace all geometric isomers, i.e. not only the 6E but also the 6Z form, especially the isomers of the formulae

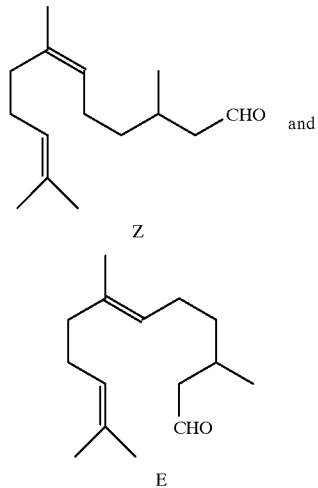

and—although usually present as the racemate—also the optical antipodes which occur by virtue of the asymmetric center in position 3.

Compound I is known and can be produced in a manner which will be known to a person skilled in the art, for example by hydrogenating farnesal in a manner known per se. The production of the individual isomers can also be effected in a manner known per se, e.g. from Z- or E-geranylacetone.

The compound of formula I used in accordance with the invention as an odorant and/or flavorant is distinguished by pleasant, flowery notes.

The most preferred 6-(E)-2(3)-dihydrofarnesal exhibits a fresh-flowery, aldehydic fragrance which is reminiscent of lily of the valley and other flowers and which can be associated readily with fresh water, ozone, sea etc. The fragrance characteristics of the E isomer are also found in the smell of the flowers of certain lily varieties, citrus varieties, orchid varieties, representatives of the Apocynaceae family, representatives of the Asclepiadaceae family and cacti varieties.

The corresponding 6-(Z) isomer exhibits similar olfactory properties, although the intensity is somewhat lower and, moreover, the overall odor is somewhat less fresh. Accordingly, in place of the pure (E)-2(3)-dihydrofarnesal there can also be used the mixture of the Z and E forms which is readily available synthetically.

Having regard to these olfactory properties, I is suitable— as a mixture or as the E or Z form—for use in the creation of the widest variety of perfume types. Flowery compositions, which by the addition of I take on a pleasant, very natural freshness and, moreover, now become much more rounded-off, represent an especially important field of use. In this connection, it has surprisingly been found that perfume products having characteristic fragrance notes, whose harmonic incorporation into a composition often presents difficulties, are easier to handle when used together with 2(3)-dihydrofarnesal and, moreover, can be used in higher concentration.

The 2(3)-dihydrofarnesals I also exhibit very interesting and valuable properties in compositions which are characterized by woody, hesperidin-like, green-herby, green-fruity, fruity, spicy, ambra-like and musk-like notes. Quite generally it can be said that compound I has a very high integration capacity in perfume compositions and therefore can be used over a broad concentration range. However, in general, the concentration used varies between about 0.1 and about 40%, preferably between about 3 and about 20%. Unless otherwise stated, percentages are by weight of the total composition.

The compound of formula I used in accordance with the invention as an odorant and/or flavorant is thus distinguished, as mentioned, by pleasant notes. Compound I combines with numerous known odorant ingredients of natural or synthetic origin, whereby the range of natural raw materials can embrace not only readily-volatile but also moderately-volatile and difficulty-volatile components and that of the synthetics can embrace representatives from practically all classes of substance, as will be evident from the following compilation:

Natural products: Basil oil, tree moss absolute, mugwort oil, bergamot oil, cassia oil, cassis bud absolute, cedarwood oil, ciste labdanum, civet, coriander oil, oak moss, elemi oil, pine needle oil, galbanum, geranium oil, clove oil, jasmine absolute and its synthetic substitute, jonquil absolute, camomile oil, labdanum, lavender oil, mandarin oil, mastix absolute, mentha citrata oil, myrrh oil, palmarosa oil, patchouli oil, petitgrain oil Paraguay, rose oil, sandalwood oil, thyme oil, vassoura oil, styrax, birch tar, vetiver oil, frankincense, ylang—ylang oil, citrus oil, cinnamon bark oil.

Alcohol: Citronellol, Dimetol® (2,6-dimethyl-heptan-2-ol), geraniol, cis-3-hexanol, linalool, Nonadyl® (6,8-dimethyl-nonan-2-ol), phenylethyl alcohol, rhodinol, Sandela® (3-isocamphyl-5-cyclohexanol), Sandalore® (3-methyl-5 (2',2',3'-trimethyl-cyclopenta-3'-en-1'-yl)-pentan-2-ol), terpineol, etc.

Aldehydes: α-Amylcinnamaldehyde, cyclamen aldehyde, decanal, phenylacetaldehyde, dodecanal, heliotropin, α-hexyl-cinnamaldehyde, hydroxycitronellal, lyral, Adoxal® (2,6,10-trimethyl-9-en-1-al), undecanal, ω-undecylenaldehyde, anis-aldehyde, vanillin, etc.

Ketones: Isoraldeine® (isomethyl a-ionone), α-ionone, β-ionone, 3-phenylisocaranone, Vertofix® (=acetylated cedarwood oil), p-methyl-acetophenone, β-damascone, geranylacetone, muscone, dihydro-β-ionone, etc.

Ester: Ethyl acetoacetate, amyl salicylate, benzyl acetate, cedryl acetate, cinnamyl formate, citronellyl acetate, geranyl acetate, cis-3-hexenyl acetate, cis-3-hexanyl benzoate, linalyl acetate, linalyl anthanilate, methyl dihydrojasmonate, Methambrat® (1-acetoxy-1-methyl-2-sec.-butylcyclohexane), Myraldylacetat® (4-(4-methyl-3-pentenyl)-cyclohex-3-en-1-yl-carbinyl acetate), phenoxyethyl isobutyrate, phenylethyl tiglate, cis-3-hexenyl salicylate, styrallyl acetate, terpenyl acetate, ethyl 2,3,6,6-tetramethyl-cyclohexy-2-ene-carboxylate, vetivenyl acetate, ortho-tert.-butylcyclohexyl acetate, etc.

Various: Coumarin, epoxycedrene, eugenol, Fixolide® (1,1,2,4,4,7-hexamethyl-6-acetyl-1,2,3,4-tetrahydronaphthalene), Galaxolid® (1,3,4,6,7,8-hexahydro-4,6,6,7,8,8-hexamethyl-cyclopentyl-γ-2-benzopyran), heliotropin, indole, indolene, isoeugenol, isobutylquinoline, jasmonyl (1,3-diacetoxy-nonane), limonene, p-menthane-8-thiol-3-one, Madrox® (1-methyl-cyclododecyl methyl ether), methyleugenol, Musk 174® (12-oxahexadecanolide), γ-nonalactone, α-undecalactone, ω-penta-decanolide, Shiff's bases, e.g. from methyl anthranilate and aldehydes which are usual in perfumery, etc.

The compound of formula I can be used in wide limits which can extend in compositions, for example, from 0.1 (detergents)–40 wt. % (alcoholic solutions), without these values being, however, limiting values, since the experienced perfumer can also produce effects with even lower concentrations or can synthesize novel complexes with even higher dosages. The preferred concentrations range between 3 and 20%. The compositions produced with I can be used for all kinds of perfumed consumer goods (Eau de Cologne, eau de toilette, extracts, lotions, creams, shampoos, soaps, salves, powders, toothpastes, mouth washes, deodorants, detergents, etc.).

Compound I can accordingly be used in the manufacture of compositions and—as will be evident from the above compilation—a broad range of known odorants or odorant mixtures can be used. In the production of such compositions the known odorants or odorant mixtures set forth above can be used according to methods known to the perfumer such as, e.g. from W. A. Poucher, Perfumes, Cosmetics, Soaps 2, 7th Edition, Chapman and Hall, London 1974.

The compound of formula I is also excellently suited for use in flavors of a wide variety.

As a flavorant, compound I can be used, for example, for rounding-off, improving, intensifying, enhancing the fresh effect and modifying (citrus) fruit flavors, e.g. apricot, peach, mango, guava, passion fruit, pineapple and banana flavors. However, herb flavors also come into consideration. As fields of use for these flavors there come into consideration, for example, foods (yoghurt, confectionery etc.), consumables taken for pleasure (tea, etc.) and drinks (lemonade etc.).

The pronounced flavor qualities of compound I (fresh flowery note with an aldehydic aspect which can combine well with the widest variety of fruit notes) enables it to be used as a flavorant in low concentrations. A suitable dosage embraces, for example, the range of 0.1 ppm–100 ppm, preferably the range of 0.5 ppm–50 ppm, in the finished product, i.e. the flavored food, consumable taken for pleasure or drink.

In the flavoring of, for example, mouth care agents the dosage can, however, also be higher and can embrace a wider range, for example the range of 1 to 1000 ppm, preferably 30–100 ppm.

The compound can be mixed with ingredients used for flavoring compositions or added to such flavorants in the usual manner. Under the flavorants used in accordance with the invention there are to be understood flavorant compositions which can be diluted or distributed in edible materials in a manner known per se. They contain, for example, about 0.1–10, especially 0.5–3 wt. %. They can be converted according to methods known per se into usual forms of use such as solutions, pastes or powders. The products can be spray-dried, vacuum-dried or lyophilized.

The known flavoring substances conveniently used in the production of such flavorants are either contained in the above compilation or can be concluded readily from the literature, such as e.g. J. Merory, Food Flavorings, Composition, Manufacture and Use, Second Edition, The Avi Publishing Company, Inc., Westport, Conn. 1968, or G. Fenaroli, Fenroli's Handbook of Flavor Ingredients, Second Edition, Volume 2, CRC Press, Inc. Cleveland, Ohio, 1975.

For the production of such usual forms of use there come into consideration, for example, the following carrier materials, thickeners, flavor enhancers, spices and auxiliary ingredients, etc.:

Gum arabic, tragacanth, salts or brewer's yeast, alginates, carrageen or similar absorbents; indoles, maltol, dienals, spice oleoresins, smoke flavors; cloves, diacetyl, sodium citrate, monosodium glutamate, disodium inosine-5'-monophosphate (IMP), disodium guanosine (sic)-5-phosphate (GMP); or special flavorants, water, ethanol, propylene (sic) glycol, glycerol, etc.

EXAMPLE 1

Production of dihydrofarnesal I 110.0 g (0.50 mol) of farnesal (mixture of 4 isomers) dissolved in 850 ml of ethanol were hydrogenated in the presence of 30 g of Raney-nickel at normal pressure until the theoretical amount of hydrogen had been taken up. Care was taken by external cooling that the reaction temperature was between 15 and 20° C. After separating the Raney-nickel 90% of the ethanol was distilled off; the concentrate was taken up in 500 ml of hexane, the hexane phase was washed with water, saturated soda solution and saturated sodium chloride solution, dried and concentrated. Distillation of the thus-obtained crude product (116.7 g) over a 20 cm Widmer column gave 79.9 g (72%) of olfactorily pleasing 6-(Z) and 6-(E)-dihydrofarnesal (~2:3) of b.p.$_{0.05}$ 98–99° C.

Mass spectrum of 6-(Z)-2(3)-dihydrofarnesal. 222(M$^+$; 0.2), 179(7), 161(4), 123(9), 109(13), 93(8), 81(14), 69(100), 55(11), 41(44).

Mass spectrum of 6-(E)-2(3)-dihydrofarnesal. 222(M$^+$; 0.4), 179(7), 161(6), 123(13), 109(18), 93(9), 81(13), 69(100), 55(15), 41(46).

EXAMPLE 2

Perfumery accord of flowery direction containing I

| | Parts by weight | |
|---|---|---|
| | (1) | (2) |
| cis-3-Hexenol | 1 | 1 |
| cis-3-Hexenyl acetate | 1 | 1 |
| Lemon oil, Italian | 10 | 10 |
| Linalool | 200 | 200 |
| Nerolidol | 100 | 100 |
| Benzyl acetate | 50 | 50 |
| Methyl benzoate | 20 | 20 |
| Cinnamic alcohol | 40 | 40 |
| Cinnamyl acetate | 50 | 50 |
| Nerol | 70 | 70 |
| Geraniol | 20 | 20 |
| Geranyl acetate | 20 | 20 |
| β-Ionone | 5 | 5 |
| Eugenol | 6 | 6 |

-continued

| | Parts by weight | |
|---|---|---|
| | (1) | (2) |
| cis-3-Hexenyl benzoate | 15 | 14 |
| cis-3-Hexenyl salicylate | 30 | 30 |
| Methyl jasmonate | 50 | 50 |
| Benzyl benzoate | 100 | 100 |
| ω-Pentadecanolide | 50 | 50 |
| 2(3)-Dihydrofarnesal (Example 1) | — | 100 |
| Dipropylene glycol | 162 | 62 |
| Total | 1000 | 1000 |

The above perfumery accord (1) was characterized by aromatic-flowery aspects and was reminiscent, for example, of ylang—ylang, Brunfelsia varieties and night-active Nicotiana varieties. Addition of 100 parts of I conferred to this accord a very valuable fresh-flowery note, which was very natural and reminiscent of damp petals. On the other hand, this valuable note could not be achieved at all by the equivalent addition of, for example, farnesal.

EXAMPLE 3

Perfumery accord of flowery direction with tea-like, spicy and herby aspects

| | Parts by weight | |
|---|---|---|
| | (1) | (2) |
| Linalool | 200 | 200 |
| Bergamot oil | 100 | 100 |
| Phenylethyl alcohol | 100 | 100 |
| Citronellol | 80 | 80 |
| Geranylacetone | 50 | 50 |
| cis-3-Hexenyl benzoate | 50 | 50 |
| Anethol | 15 | 15 |
| Anisaldehyde | 5 | 5 |
| Methyl jasmonate | 30 | 30 |
| Methyl dihydro jasmonate | 40 | 40 |
| α-Terpineol | 30 | 30 |
| Geraniol | 20 | 20 |
| β-Ionone | 15 | 15 |
| Dihydro-β-ionone | 15 | 15 |
| Eugenol | 5 | 5 |
| Phenylacetaldehyde | 5 | 5 |
| Citral | 5 | 5 |
| 2(3)-Dihydrofarnesal (Example 1) | — | 60 |
| Dipropylene glycol | 235 | 175 |
| | 1000 | 1000 |

The above perfumery accord (1), which had a basic flowery character, was characterized by additional tea-like, spicy and herby aspects. Addition of 60 parts of I brang about a clear improvement of this accord in that the tea-like and spicy notes were then combined with the flowery base note in an optimum manner. The thus-obtained accord 2 became significantly more harmonic, had a substantially stronger radiance and was distinguished by an additional very pleasant fresh-flowery note. The accord could also be used for modifying flavors. Such an improvement in the accord could in no manner be achieved by the addition of, for example, farnesal.

I claim:

1. An odorant composition, comprising from about 0.1 to about 40 wt. % 2(3)-dihydrofarnesal of the formula

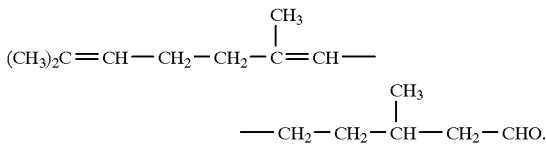

2. The odorant composition of claim 1, wherein the 2(3)-dihydrofarnesal is a 6-(E) isomer of formula I.

3. The odorant composition of claim 1, wherein the 2(3)-dihydrofarnesal is a 6-(Z) isomer of formula I.

4. The odorant composition of claim 1, wherein the 2(3)-dihydrofarnesal of formula I is present in an amount from about 3 to about 20 wt. %.

5. A flavored food product comprising from about 0.1 to about 100 ppm of the dihydrofarnesal compound recited in claim 1.

6. The flavored food product of claim 5 wherein the 2(3)-dihydrofarnesal of formula I is present in an amount of from about 0.5 to about 50 ppm.

7. The flavored food product of claim 6 wherein the 2(3)-dihydrofarnesal is a 6-(E) isomer of formula I.

8. The flavored food product of claim 6 wherein the 2(3)-dihydrofarnesal is a 6-(Z) isomer of formula I.

9. A flavored mouth care product comprising from about 1 to about 1000 ppm of the dihydrofarnesal compound recited in claim 1.

10. The flavored mouth care product of claim 9 wherein the 2(3)-dihydrofarnesal of formula I is present in an amount from about 30 to about 100 ppm.

11. The flavored mouth care product of claim 10 wherein the 2(3)-dihydrofarnesal is a 6-(E) isomer of formula I.

12. The flavored mouth care product of claim 10 wherein the 2(3)-dihydrofarnesal is a 6-(Z) isomer of formula I.

13. A flavorant composition for incorporation into food products or mouth care products comprising from about 0.1 to about 10 wt. % of the dihydrofarnesal compound recited in claim 1.

14. The flavorant composition of claim 13 wherein the 2(3)-dihydrofarnesal of formula I is present in an amount from about 0.5 to about 3 wt. %.

15. The flavorant composition of claim 13 wherein the 2(3)-dihydrofarnesal is a 6-(E) isomer of formula I.

16. The flavorant composition of claim 13 wherein the 2(3)-dihydrofarnesal is a 6-(Z) isomer of formula I.

17. A method of improving an odorant composition comprising adding an organoleptically effective amount of 2(3)-dihydrofarnesal of the formula

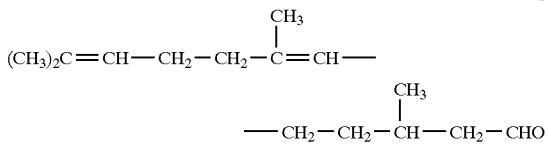

to said odorant composition.

18. A method of improving a flavorant composition comprising adding an organoleptically effective amount of the dihydrofarnesal compound recited in claim 17 to said flavorant composition.

19. A method of improving a food product comprising adding an organoleptically effective amount of the dihydrofarnesal compound recited in claim 17 to said food product.

* * * * *